(12) United States Patent
Amselem et al.

(10) Patent No.: US 11,484,516 B2
(45) Date of Patent: Nov. 1, 2022

(54) AGENTS FOR INCREASING MEIBOMIAN GLAND LIPID SECRETION

(71) Applicant: Azura Ophthalmics Ltd., Tel Aviv (IL)

(72) Inventors: Shimon Amselem, Tel Aviv (IL); Yair Alster, Tel Aviv (IL); Doron Friedman, Tel Aviv (IL); Omer Rafaeli, Tel Aviv (IL)

(73) Assignee: AZURA OPHTHALMICS LTD., Tel Aviv (IL)

( * ) Notice: Subject to any disclaimer, the term of this patent is extended or adjusted under 35 U.S.C. 154(b) by 0 days.

(21) Appl. No.: 16/498,299

(22) PCT Filed: Mar. 28, 2018

(86) PCT No.: PCT/IB2018/000415
§ 371 (c)(1),
(2) Date: Sep. 26, 2019

(87) PCT Pub. No.: WO2018/178769
PCT Pub. Date: Oct. 4, 2018

(65) Prior Publication Data
US 2020/0030268 A1    Jan. 30, 2020

Related U.S. Application Data

(60) Provisional application No. 62/478,501, filed on Mar. 29, 2017.

(51) Int. Cl.
| A61K 31/19 | (2006.01) |
| A61P 27/02 | (2006.01) |
| A61K 9/00 | (2006.01) |
| A61K 45/06 | (2006.01) |

(52) U.S. Cl.
CPC ............ *A61K 31/19* (2013.01); *A61K 9/0014* (2013.01); *A61K 9/0048* (2013.01); *A61K 45/06* (2013.01); *A61P 27/02* (2018.01)

(58) Field of Classification Search
CPC .... A61K 31/19; A61K 9/0014; A61K 9/0048; A61K 45/06; A61K 31/325; A61P 27/02
See application file for complete search history.

(56) References Cited

U.S. PATENT DOCUMENTS

| 2009/0238810 A1 | 9/2009 | Nyunt |
| 2011/0104206 A1* | 5/2011 | Nanduri ................ A61K 31/19 |
| 2011/0218241 A1 | 9/2011 | Preston et al. |
| 2015/0190279 A1 | 7/2015 | Acharya et al. |
| 2016/0106775 A1 | 4/2016 | Alster et al. |

FOREIGN PATENT DOCUMENTS

| JP | H069383 A | 1/1994 |
| JP | H1171272 A | 3/1999 |
| JP | 2016520335 A | 7/2016 |
| WO | WO-2013003731 A2 | 1/2013 |
| WO | WO-2016063130 A1 | 4/2016 |
| WO | WO-2017055924 A2 | 4/2017 |
| WO | WO-2018178769 A1 | 10/2018 |

OTHER PUBLICATIONS

Yanagi Bucillamine Suppresses CNV, Ophth. & Vis. Sci. November p. 3495 (Year: 2002).*
Barrault et al. Immortalized sebocytes can spontaneously differentiate into a sebaceous-like phenotype when cultured as a 3D epithelium. Exp Dermatol 21:299-319 (2012).
Berge et al. Pharmaceutical Salts. Journal of Pharmaceutical Sciences 66(1):1-19 (Jan. 1977).
Chew et al. An instrument for quantifying meibomian lipid on the lid margin: the Meibometer. Curr Eye Res 12(3):247-254 (1993).
Heiligenhaus et al. Therapy of dry eye disorders [Therapie von Benetzungsstorungen]. Klin Monatsbl Augenheilkd 204:162-168 (1994) (English Summary).
PCT/IB2018/000415 International Search Report and Written Opinion dated Aug. 30, 2018.
Akyol-Salman et al. Efficacy of topical N-acetylcysteine in the treatment of meibomian gland dysfunction. J Ocul Pharmacol Ther 26(4):329-333 (2010).

* cited by examiner

*Primary Examiner* — Matthew P Coughlin
*Assistant Examiner* — Thurman Wheeler
(74) *Attorney, Agent, or Firm* — Wilson Sonsini Goodrich & Rosati

(57) ABSTRACT

Described herein are compositions and methods for the increasing the quantity of lipids secreted from meibomian glands. Such compositions and methods are useful for the treatment of meibomian gland dysfunction and disorders resulting therefrom.

16 Claims, 5 Drawing Sheets

AGENTS FOR INCREASING MEIBOMIAN GLAND LIPID SECRETION

CROSS-REFERENCE TO RELATED APPLICATIONS

This application is a U.S. National Entry Application of International Application No. PCT/IB2018/000415, filed internationally on Mar. 28, 2018, which claims the benefit of U.S. Provisional Application No. 62/478,501, filed on Mar. 29, 2017, which are incorporated by reference herein in their entirety.

BACKGROUND OF THE INVENTION

Meibomian glands are glands arranged vertically within the eyelid near the lashes. The force of an eyelid blink causes oil to be excreted onto the posterior lid margin. The oil is the "staying power" of the tears that helps prevent rapid tear evaporation. In a patient with Meibomian gland dysfunction (MGD), vision is affected because there is too much or too little oil in the tear film.

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The eyelid margin is the source of physiologically important lipid secretion, meibum. The eyelid meibomian gland secretions form the outer layer of the tear film. Functions which have been attributed to this tear film lipid layer are: (1) a lubricant facilitating the movement of the eyelids during a blink, (2) a barrier preventing evaporation of the aqueous tear fluid, and (3) a barrier to the entry of microorganisms and organic matter such as pollen.

The moving eyelids spread meibum across the ocular surface and mix it with aqueous tears (AT), which are produced by lacrimal glands. Mixing and spreading of meibum and AT result in a near-continuous structure called tear film (TF), which covers the entire ocular surface and serves multiple purposes, including protective, lubricatory, nutritional, and antimicrobial, among others. TF was also linked to visual acuity because it provides a smoother ocular surface which improves the optical properties of the eye.

However, TF is not homogeneous, which is not surprising considering that lipids do not easily form aqueous solutions and tend to separate by forming a clearly hydrophobic lipid-enriched sub-phase. A classical view on the TF structure presumes a three-layer organization of TF. As lipids are, typically, less dense than water, they accumulate on the surface of the aqueous sub-phase thus forming a lipid-enriched outer-most layer of TF (also called tear film lipid layer, or TFLL). Beneath the TFLL is a much more hydrophilic aqueous layer enriched with water-soluble proteins, carbohydrates, salts, and other more or less hydrophilic compounds. The closest to the corneal epithelium is believed to be a relatively hydrophilic mucin-enriched glycocalyx layer, which is formed primarily of membrane-bound mucins. By using interferometry, the depth of TFLL was estimated to be ~40-90 nanometers, while the aqueous layer was found to be much thicker at about 4 micrometers. It is important to realize that all three layers are soft and dynamic structures, where changes occur as a result of numerous simultaneously manifesting factors, e.g. mechanical movements of the eyelids, continuous secretion of meibum, aqueous tears and mucins, and AT evaporation and drainage through nasal ducts. If the eye is forced to stay open without blinking, the human TF quickly deteriorates, thins, and breaks—a phenomenon known as tear break-up.

The tear break-up time (TBUT) for humans is measured in seconds. It has long been considered an important and objective diagnostic parameter in evaluating the health of the ocular surface. TBUT is widely used in ophthalmic practice to diagnose dry eye—a multifactorial condition (or disease) whose onset and progress is linked to the deterioration of TF in general, and TFLL in particular. When the break-up occurs, the cornea becomes exposed to air, causing a discomfort to the patient. The incomplete coverage of the ocular surface with TF also increases the chances of damage to the corneal epithelium cells because of excessive dehydration, abrasions, irritation, inflammation, infections, etc. Another cause of the TF instability are meibomian glands incapable of secreting enough meibum of the necessary quality, e.g. because of MGD associated with meibomian gland inflammation and/or obstruction.

Lipids produced by the meibomian glands are the main component of the superficial lipid layer of the tear film that protects it against evaporation of the aqueous phase and is believed also to stabilize the tear film by lowering surface tension. Alterations of the lipid phase more frequently point to MGD than alterations in isolated aqueous phase, as reported in a study by Heiligenhaus et al. (Heiligenhaus et al., Therapie. von Benetzungsstorungen. Klin. Monatsbl. Augenheilkd., 1994, Vol. 204, pages 162-168) where it was observed that a lipid deficiency occurred in 76.7% of dry eye patients compared with only 11.1% of those with isolated alterations of the aqueous phase. Hence, meibum lipids are essential for the maintenance of ocular surface health and integrity.

Lipids are the major components of meibum (also known as "meibomian gland secretions"). The biochemical composition of meibum is extremely complex and very different from that of sebum. Lipids are universally recognized as major components of human and animal meibum. In humans, more than 90 different proteins have been identified in meibomian gland secretions. A large number of investigators have attempted to characterize the meibum, and there has been a large range of amounts of lipids recovered by investigators (Table 1), the likely cause being the use of different collection and analysis techniques.

TABLE 1

Type and Amount of Each Lipid Present in the Meibum.

| Lipid | Polarity | Amount |
|---|---|---|
| Free Fatty Acids | Non-Polar | 0.0-10.4% |
| Wax Esters | Non-Polar | 28.0-68.0% |
| Cholesterol Esters | Non-Polar | 0.0-39.0% |
| Diesters | Non-Polar | 2.3-17.6% |
| Free sterols | Non-Polar | Trace-30.0% |
| Monoglycerides | Non-Polar | Trace-2.6% |
| Diglycerides | Non-Polar | Trace-3.3% |
| Triglycerides | Non-Polar | Trace-9.0% |
| Fatty Acid Amides | Non-Polar | Unknown |
| Hydrocarbons | Non-Polar | Trace-7.5% |
| Phospholipids | Polar | 0.0-14.8% |
| Sphingolipids | Polar | Unknown |
| ω-Hydroxy Fatty Acids | Polar | Unknown |

In subjects without MGD, the meibum lipid is a pool of clear oil. In MGD, the quantity, quality and composition of the secreted material is altered. Thus, MGD is characterized by lipid deficiency. Further, in MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a meibum lipids of increased viscosity.

Lipid deficiency and increased viscosity of meibum are important pathogenic factors in MGD and are observed in majority of cases of obstructive MGD. Therefore it is highly desired to enhance lipogenesis and lipid secretion from the meibomian gland, to overcome lipid deficiency as well as reduce the viscosity of meibum oil composition which allows for dissolution of any obstruction of the meibomian gland.

Highly viscous meibum is mixed with hyperkeratotic cell material, as seen in expressed pathologic human meibum prepared as smears or in impression cytology and in histopathology, as verified by molecular biology and immunohistochemistry. Increased viscosity has also been observed inside the obstructed glands of animal models. It is therefore desirable to soften and liquefy the obstructing lipids in order to open the duct and restore normal flow of excreted lipids.

Meibomian gland dysfunction, or MGD, is a leading contributor of dry eye syndrome, and is often characterized by insufficient lipid delivery, by the meibomian gland, to the surface of the eye. MGD, also termed posterior blepharitis, is the most common form of lid margin disease. In the early stages, patients are often asymptomatic, but if left unmanaged, MGD can cause or exacerbate dry eye symptoms and eyelid inflammation. The oil glands become blocked with thickened secretions. Chronically clogged glands eventually become unable to secrete oil which results in permanent changes in the tear film and dry eyes. Symptoms of MGD include eye dryness, burning sensation, itching, stickiness, watering, sensitivity to light, red eyes, and blurred vision.

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye.

MGD is not synonymous with posterior blepharitis, which describes inflammatory conditions of the posterior lid margin. MGD may cause posterior blepharitis, but MGD may not always be associated with inflammation or posterior blepharitis. Clinical signs of MGD include meibomian gland dropout, altered meibomian gland secretion, and changes in lid morphology.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction or qualitative or quantitative changes in the glandular secretion (decreased meibum expression by moderate digital pressure).

Currently, standard treatment to MGD is somewhat limited to heating the lids to increase oil production and melt the oil that has solidified in the glands by warm compresses, applying light pressure to the lid margin near the lash line, and manually removing the thickened secretions as well as pharmacological treatments like antibiotics and anti-inflammatory agents. However, these treatments may be frustrating to patients and ophthalmologists. Massage of the eyelid provides only partial and temporary relief of obstruction of the meibomian glands and this could be painful. Conventional approaches for warm compresses apply heat to the outer surface of the eyelid; therefore the heat is frequently of limited effectiveness. The use of topical antibiotics and corticosteroids to suppress the bacterial colonization and inflammation of the eyelid margin associated with MGD has been shown to be effective in the relief of symptoms and the signs of MGD, however, the success of this treatment may have nothing to do with the changed meibum. Antibiotics, particularly the tetracyclines (including doxycycline, tetracycline, and minocycline) and azithromycin are used to suppress bacterial colonization and reduce inflammation of the lid margin; however, drug intolerance and prolonged therapy have limited the clinical application of oral antibiotics.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, Q-tip, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks.

In summary, each of these treatments has a different shortcoming and the treatment of MGD remains challenging. Therefore, methods are needed to improve patient comfort, which will not cause harm to the meibomian glands and canals, that will reduce the dependency on frequent office visits and improve secretion of meibum.

Emerging treatments for MGD include the use of mucolytic and/or keratolytic agents. The goal of mucolytic therapy is to facilitate physiological clearance by optimizing the viscoelasticity of mucus, while keratolytic therapy aims to soften keratin, a major component of the skin.

Despite the possible treatment options for MGD, it is still difficult to obtain complete relief of signs and symptoms.

SUMMARY OF THE INVENTION

One embodiment provides a method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent comprises a sulfhydryl group. Another embodiment provides the method wherein the agent is a bucillamine. Another embodiment provides the method wherein the agent is a compound, or a pharmaceutically acceptable salt thereof, having the structure provided below:

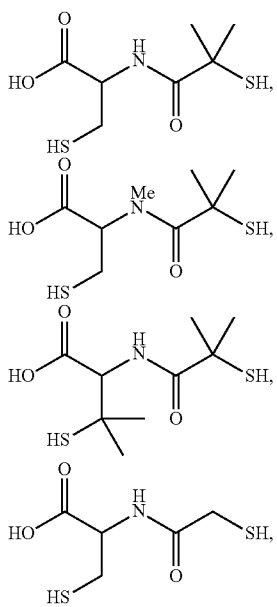

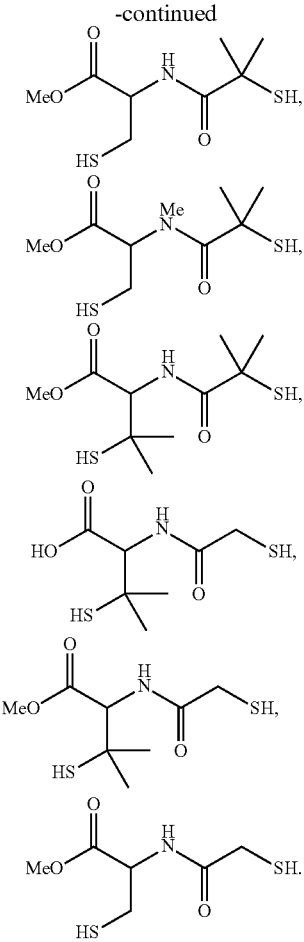

Another embodiment provides the method wherein the ophthalmically-acceptable carrier comprises at least one ophthalmically-acceptable excipient. Another embodiment provides the method further comprising the step of administering to the patient a keratolytic agent. Another embodiment provides the method wherein the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

One embodiment provides a method for treating meibomian gland dysfunction, comprising topically administering to the eyelid margin of the patient in need thereof an ophthalmic composition comprising an ophthalmically-acceptable carrier and a therapeutically-effective amount of at least one agent, wherein the agent comprises a sulfhydryl group. Another embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

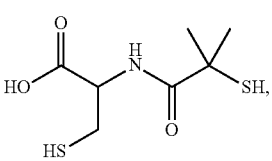

-continued

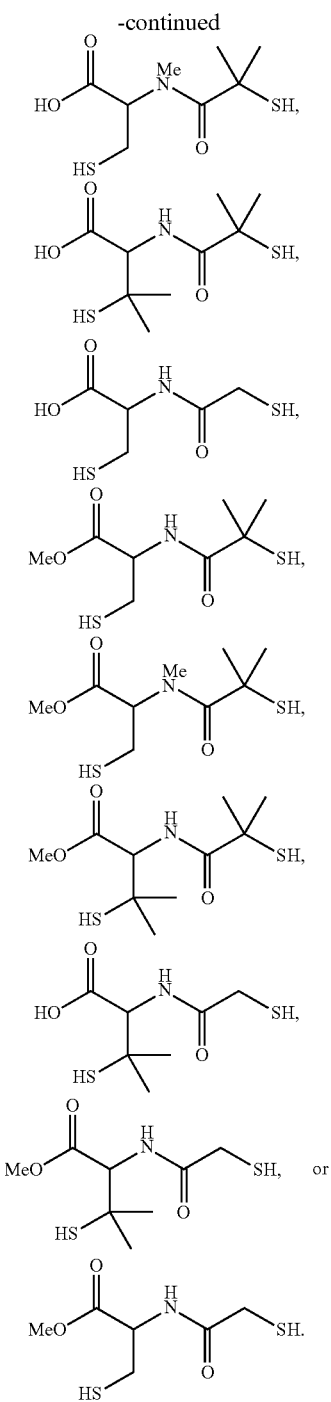

Another embodiment provides the method wherein the ophthalmically-acceptable carrier comprises at least one ophthalmically-acceptable excipient. Another embodiment provides the method further comprising the step of administering to the patient a keratolytic agent. Another embodiment provides the method wherein the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin. Another embodiment provides the method wherein the meibomian gland dysfunction is characterized by obstruction of a meibomian gland. Another embodiment provides the method wherein the topical administration of the agent to the eyelid margin of the patient is repeated until the meibomian gland obstruction is substantially removed. Another embodiment provides the method wherein the topical administration of the agent to the eyelid margin of the patient is periodically repeated to prevent formation of a meibomian gland obstruction.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
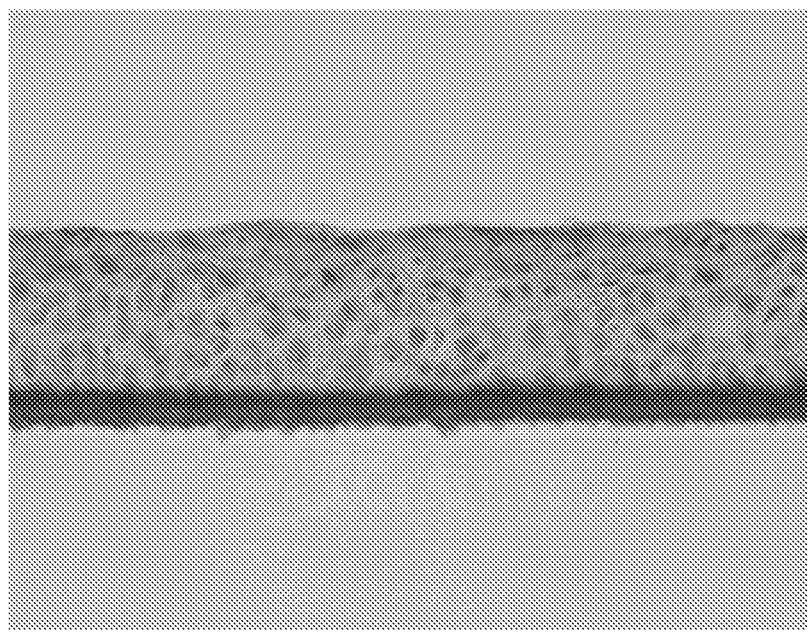
FIG. 1 is an illustration of Oil-red-O staining in 3D Sebocytes epithelium for the control.

Described herein are methods for enhancing lipogenesis and/or lipid secretion by administering a thiol-containing agent which increases the production of lipids in meibomian glands, increases the quantity of lipids secreted from meibomian glands, and/or alters the composition of lipids secreted from meibomian glands. The agents described herein include agents for acute therapies, for use, e.g., by a physician or other trained specialist, and agents for chronic therapies, e.g., either by a physician or other trained specialist, or by the patient. Certain lipogenesis and lipid secretion enhancing agents are described herein; further provided herein are methods for preparing a composition comprising lipogenesis and lipid secretion enhancing thiol-containing agents as well as their use in methods of treatment of patients.

The terms "meibomian gland dysfunction" and "MGD" as interchangeably used herein, refer to chronic, diffuse abnormality of the meibomian glands, that is characterized by terminal duct obstruction or qualitative or quantitative changes in the glandular secretion, or both. MGD may result in alteration of the tear film viscosity, eye irritation symptoms, inflammation, or ocular surface disease. The most prominent aspects of MGD are obstruction of the meibomian gland orifices and terminal ducts and changes in the meibomian gland secretions. MGD also refers to functional abnormalities of the meibomian gland, while "meibomian gland disease," describes a broad range of meibomian gland disorders, that includes neoplasia and congenital disease.

According to the principles of the present invention, thiol-containing agents which induce lipogenesis and meibum lipid secretion, can be used, e.g., as treatment for MGD through thiol-mediated lipid over-secretion mechanisms.

Drug-induced activation of cellular lipogenesis thus represents a new approach for therapeutic treatment of meibomian gland dysfunction through enhanced synthesis of cholesterol and increased production of fatty acids and triglycerides that lead to alterations in composition of the meibum lipids, by decreasing the melting point and viscosity of the meibum lipids, which results in a more fluid appearance of meibum lipids.

The lipogenesis and lipid secretion enhancing thiol-containing agents described herein are useful either as an acute therapy (e.g., by a trained specialist or physician) or as a chronic therapy (e.g., in the hands of a patient, or alternatively, by a trained specialist or physician). The agents are tested, in certain embodiments, using the assays and methods described herein (e.g., as described in the examples).

Drugs that have thiol groups have previously been reported to cause sebum over-production. Drugs containing thiol groups were also reported to cause pemphigus, a skin disease resembling seborrheic dermatitis, characterized by oily skin. Xanthine oxidoreductase (XOR) is an essential enzyme for milk lipid droplet secretion and it is known to exist in two distinct and interconvertible enzymatic forms, a thiol reduced form (XD) and a thiol oxidized form (XO), which differ in their enzymatic properties and conformations. Mammary tissue and milk fat globule membranes (MFGM) have been shown to contain a thiol oxidase that is capable of converting XD to XO. The association between XOR and the apical plasma membrane is mediated by thiol-dependent processes that involve the formation of disulphide bond cross-links with Butyrophilin protein (the most abundant protein in MFGM also essential for secretion of lipid droplets in mammary gland), ADPH or other membrane proteins, and/or conformational changes in XOR. The levels of expression and the apical membrane localization of XOR are crucial properties of secreting mammary epithelial cells and the membrane association of XOR regulates coupling of cytoplasmic lipid droplets to the apical plasma membrane during lipid secretion.

The present invention provides, in an aspect, a method for increasing lipid secretion from a meibomian gland, comprising topically administering to the eyelid margin of the patient in need thereof an ophthalmic composition comprising an ophthalmically-acceptable carrier and a therapeutically-effective amount of at least one agent which increases lipogenesis in the meibomian gland or increases lipid secretion from the meibomian gland, wherein the agent comprises a sulfhydryl group. One embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

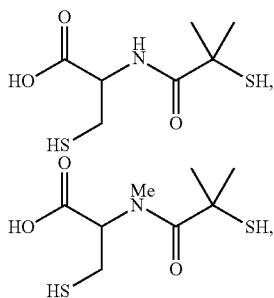

-continued

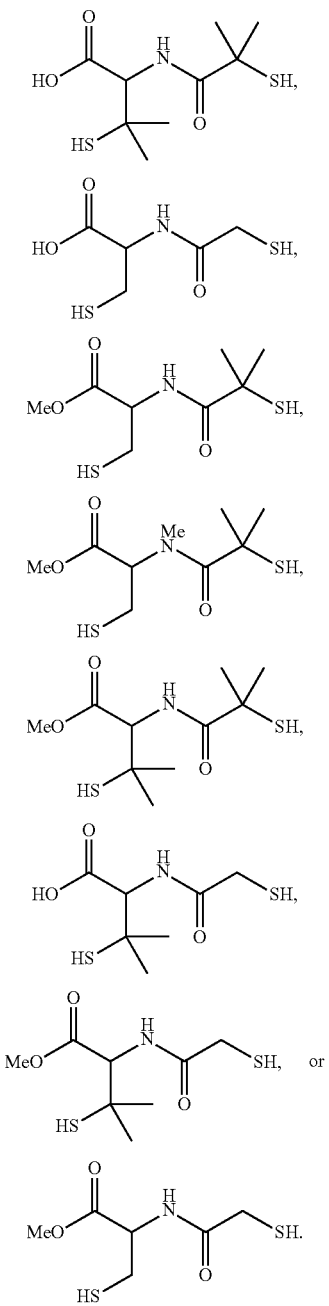

The present invention provides, in an aspect, a method for increasing lipid secretion from a meibomian gland, comprising topically administering to the eyelid margin of the patient in need thereof an ophthalmic composition comprising an ophthalmically-acceptable carrier and a therapeutically-effective amount of an agent which increases lipogenesis in the meibomian gland or increases lipid secretion from the meibomian gland, wherein the agent comprises a sulfhydryl group. One embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

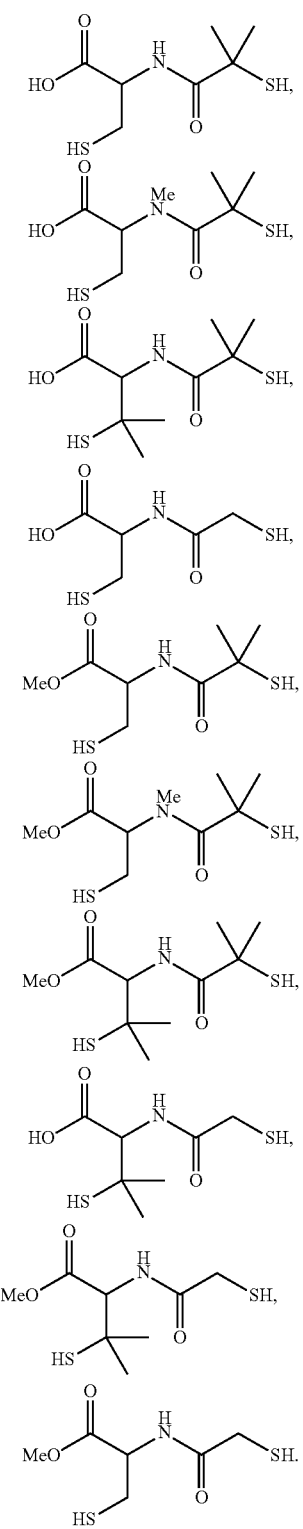

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group. One embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

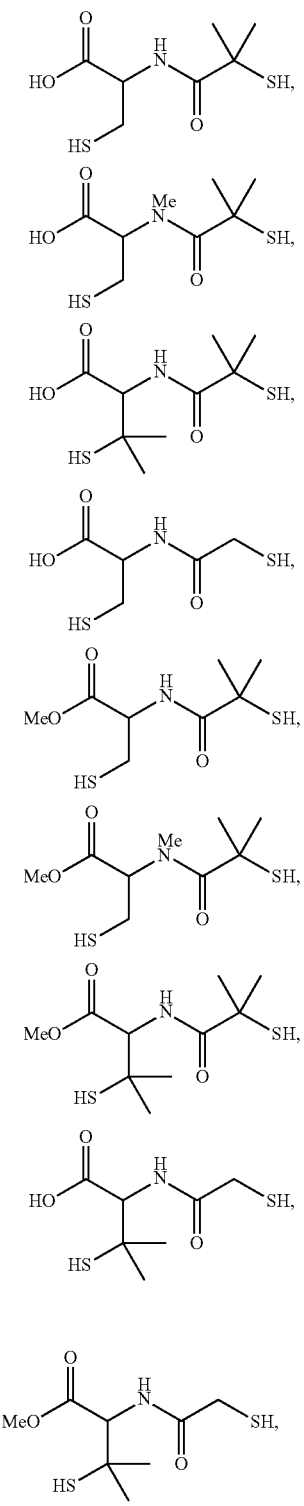

-continued

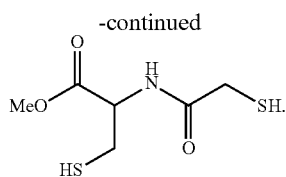

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, and wherein the ophthalmically-acceptable carrier comprises at least one ophthalmically-acceptable excipient. One embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

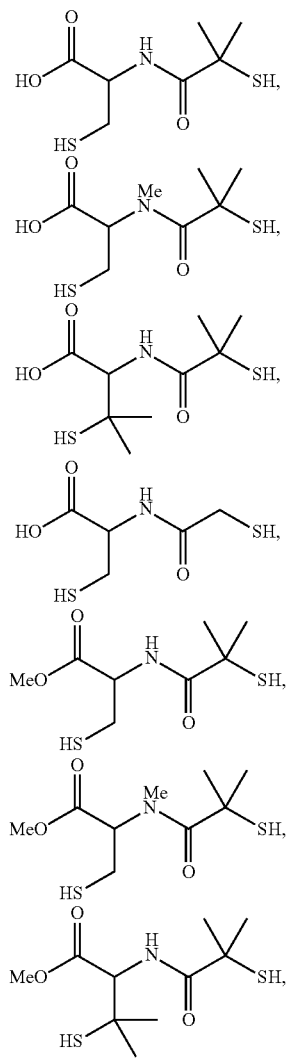

-continued

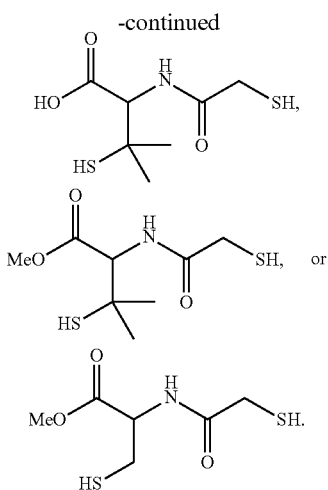

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group, and wherein the ophthalmically-acceptable carrier comprises no more than two ophthalmically-acceptable excipients. One embodiment provides the method wherein the agent is a bucillamine, or a pharmaceutically acceptable salt thereof. Another embodiment provides the method wherein the agent is a compound, or a pharmaceutically acceptable salt thereof, having the structure provided below:

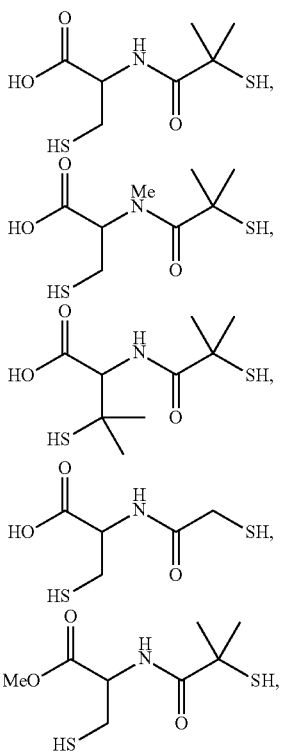

-continued

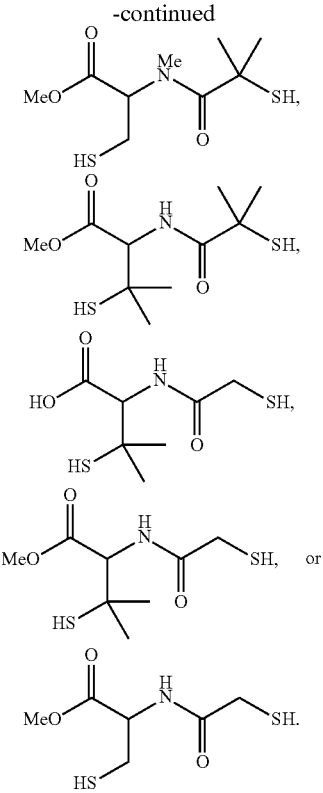

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group and wherein the ophthalmically-acceptable carrier comprises no more than three ophthalmically-acceptable excipients. One embodiment provides the method wherein the agent is a bucillamine, or a pharmaceutically acceptable salt thereof. Another embodiment provides the method wherein the agent, or a pharmaceutically acceptable salt thereof, is a compound having the structure provided below:

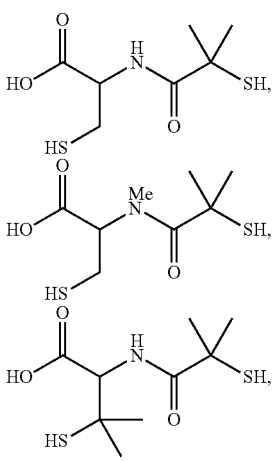

-continued

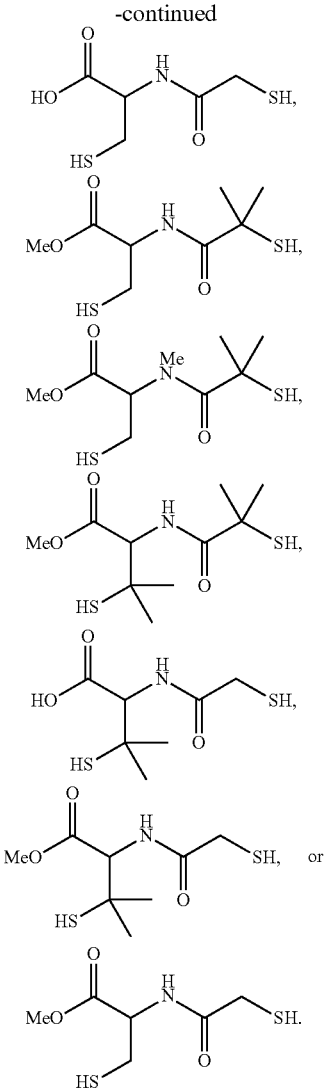

The present invention provides, in an aspect, a method for increasing lipid secretion from a meibomian gland, comprising topically administering to the eyelid margin of the patient in need thereof an ophthalmic composition consisting of an ophthalmically-acceptable carrier and a therapeutically-effective amount of an agent which increases lipogenesis in the meibomian gland or increases lipid secretion from the meibomian gland, wherein the agent comprises a sulfhydryl group and wherein the ophthalmically-acceptable carrier comprises no more than four ophthalmically-acceptable excipients. One embodiment provides the method wherein the agent is a bucillamine, or a pharmaceutically acceptable salt thereof. Another embodiment provides the method wherein the agent, or a pharmaceutically acceptable salt thereof, is a compound having the structure provided below:

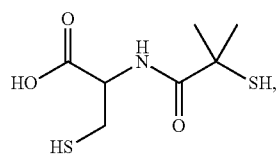

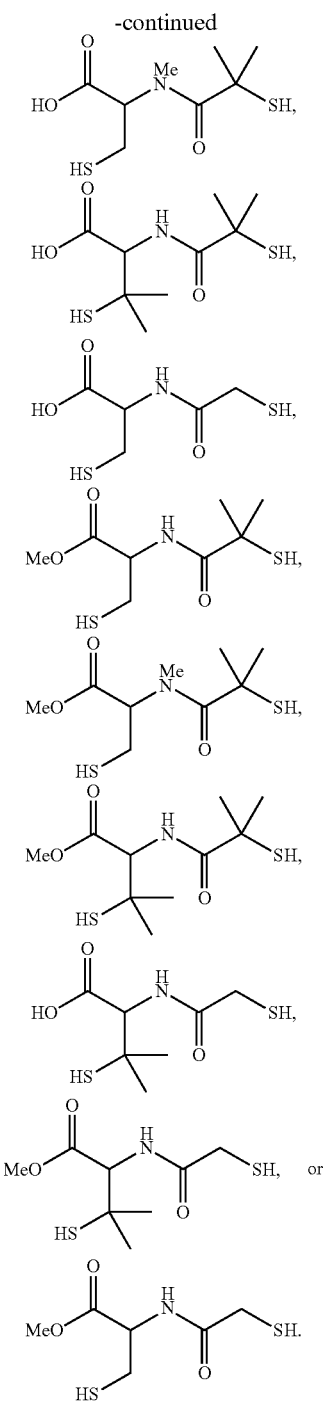

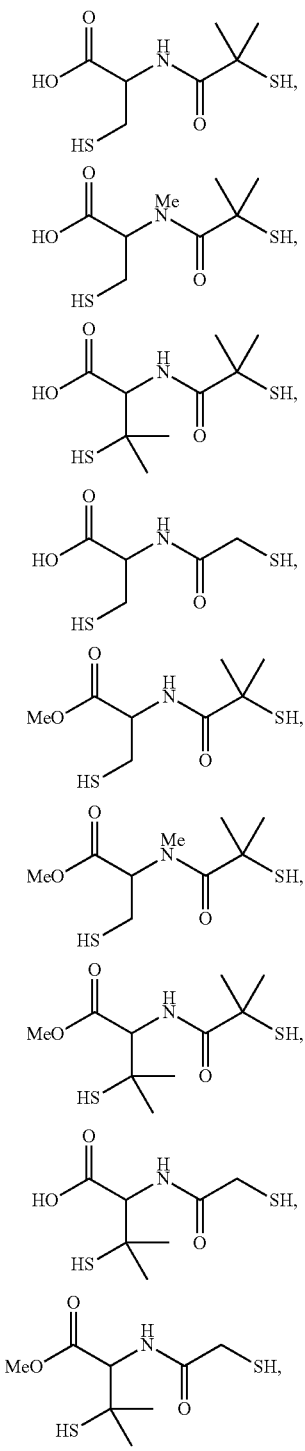

the meibomian gland or increases lipid secretion from the meibomian gland, wherein the agent comprises a sulfhydryl group and wherein the agent exhibits a lipogenic effect and a keratolytic effect. In some instances the agent exhibiting a lipogenic effect and a keratolytic effect is bucillamine, or a pharmaceutically acceptable salt thereof. In some instances, the agent exhibiting a lipogenic effect and a keratolytic effect is a compound, or a pharmaceutically acceptable salt thereof, provided below:

In certain embodiments, the methods described above further comprise the step of administering to the patient a keratolytic agent. In certain embodiments, the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

In certain embodiments, of the method for increasing lipid secretion from a meibomian gland, comprising topically administering to the eyelid margin of the patient in need thereof an ophthalmic composition comprising an ophthalmically-acceptable carrier and a therapeutically-effective amount of at least one agent which increases lipogenesis in

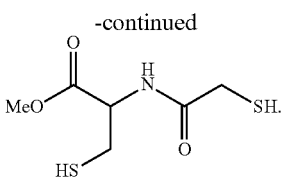

In certain embodiments, the meibomian gland dysfunction is characterized by obstruction of a meibomian gland. In certain embodiments, the topical administration of the agent to the eyelid margin of the patient is repeated until the meibomian gland obstruction is substantially removed. In certain embodiments, the topical administration of the agent to the eyelid margin of the patient is periodically repeated to prevent formation of a meibomian gland obstruction.

In certain embodiments, the methods described above result in a therapeutically effective increase in the quantity of lipids produced by the meibomian gland. In certain embodiments, the methods described above result in a therapeutically effective increase in the quantity of lipids secreted from the meibomian gland. In certain embodiments, the methods described above result in an alternation of the composition of lipids secreted by meibomian gland. In certain embodiments, the methods described above result in an alternation, preferably a reduction, of the viscosity of lipids secreted by meibomian gland.

In some embodiments, the active agents are formulated and applied such that they are acceptable to the surface of the eye (i.e. not causing undue irritation or disruption to the epithelial surface of the eye), and do not compromise lipid producing cells in contact with the composition.

In some embodiments, the composition is applied for a duration and frequency that is acceptable and practical to the physician or patient administering the agent. For example, a physician applies a composition described herein weekly or twice a week for several weeks to induce increase in the quantity of lipids secreted from the meibomian gland and the patient applies a different composition on a daily basis, or the patient uses a more potent composition on a daily basis for several weeks and then, subsequently uses a less potent composition of a daily basis thereafter. In some embodiments, the composition is applied by the patient on a daily basis once or several times a day.

In some embodiments, the method of application varies, depending on the concentration of the agent and/or the extent of lipid deficiency. In other embodiments, the method of application of the composition is tailored to enhance the penetration or residency time on the target tissue in order to enhance the effect of the treatment. In other embodiments, the method of application of the composition is varied to enhance the penetration or residency time on the target tissue to minimize the amount of application time necessary. In other embodiments, the composition is formulated (e.g., by adjusting viscosity and/or skin-adhesiveness) to increase contact with the target tissue while minimizing contact with non-target tissues, including the eye, and thus limit or reduce any undesired collateral activity.

In certain embodiments, the concentration of the agent and of the excipients is optimized to deliver the minimum effective concentration of the agent to achieve the therapeutic benefit while minimizing any ocular irritation or disruption, or irritation or disruption to surrounding ocular tissues.

The methods and compositions described herein are means for increasing the quantity of lipids secreted from meibomian glands, altering the composition of the lipids secreted by the meibomian glands, and/or reducing the viscosity of lipids secreted from meibomian glands, thereby enhancing the dissolution of any meibomian gland obstruction and improving tear breakup time (TBUT). The compositions used in the methods of the present invention include at least one lipogenesis and lipid secretion enhancing thiol-containing agent. In some embodiments, the agent is a thiol-containing drug that causes increased meibum production. In some embodiments, the agent is the thiol-containing agent bucillamine, or a pharmaceutically acceptable salt thereof.

Another embodiment provides the method wherein the agent is a compound, or a pharmaceutically acceptable salt thereof, having the structure provided below:

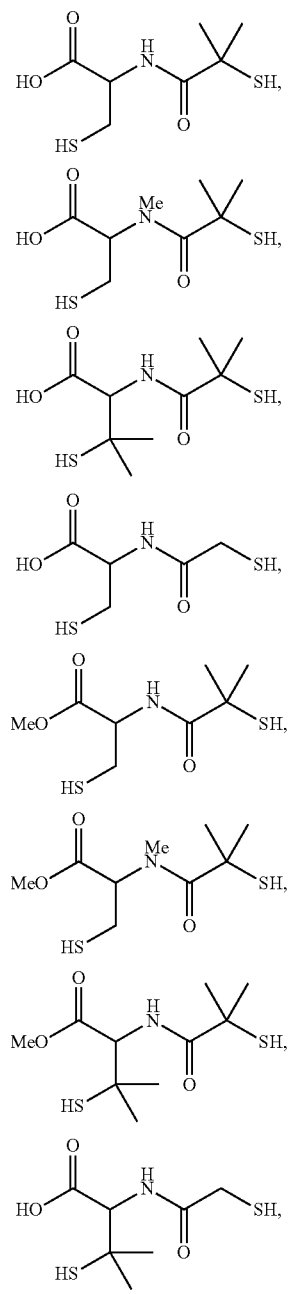

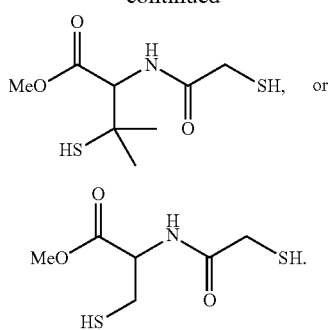

A method for increasing lipid secretion from a meibomian gland, comprising topically administering to the eyelid margin of the patient in need thereof an ophthalmic composition comprising an ophthalmically-acceptable carrier and an effective amount of at least one agent which increases lipogenesis in the meibomian gland or increases lipid secretion from the meibomian gland, wherein the agent is bucillamine, or a pharmaceutically acceptable salt thereof. Another embodiment provides the method wherein the agent is a compound, or a pharmaceutically acceptable salt thereof, having the structure provided below:

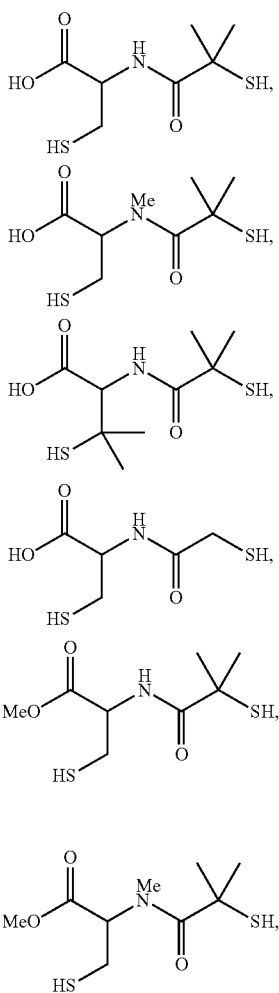

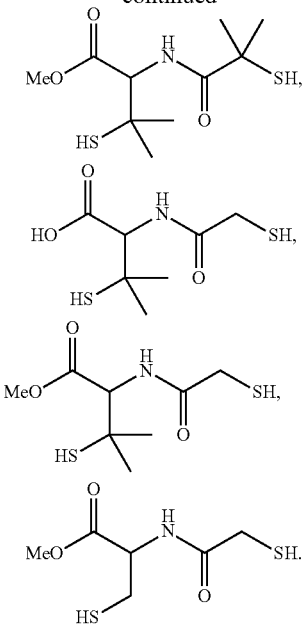

The term "maintenance therapy" or "maintenance dosing regime" refers to a treatment schedule for a subject or patient diagnosed with a disorder/disease, e.g., MGD, to enable them to maintain their health in a given state, e.g., remission.

In one embodiment, the lipid secretion enhancing thiol-containing agent used in maintenance therapy setting is bucillamine, or a pharmaceutically acceptable salt thereof. In another embodiment provides the method wherein the agent is a compound, or a pharmaceutically acceptable salt thereof, having the structure provided below:

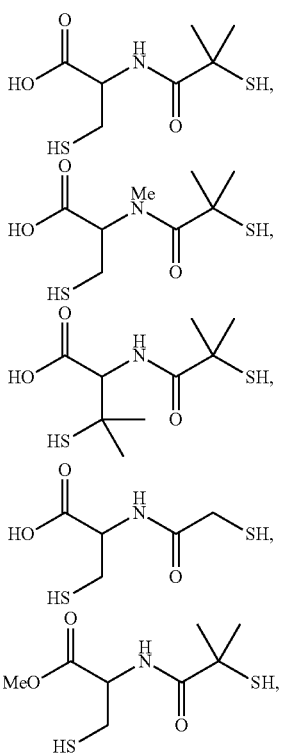

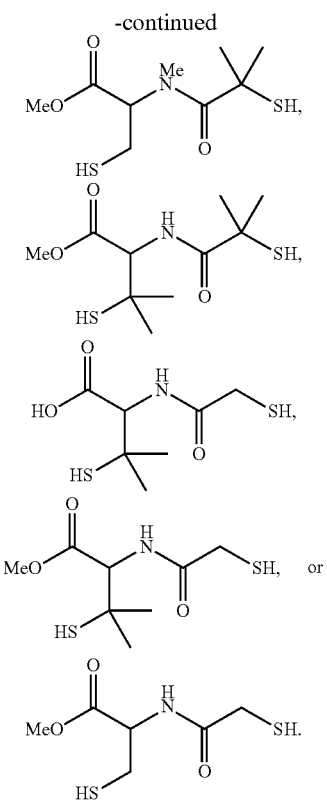

One embodiment provides a method for enhancing lipid secretion from meibomian gland in a patient in need thereof by administering a topical composition comprising a lipid secretion enhancing thiol-containing agent, wherein the composition comprises 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 5%, or 10% of lipid secretion enhancing thiol-containing agent. In some embodiments, the composition is formulated as a suspension, emulsion, cream, lotion, gel, or ointment. In some embodiments, the composition is applied as a thin layer to clean skin initially once daily on alternate days, and is then gradually increased up to twice daily as tolerance develops. In some embodiments, the composition is an ointment or paste. In some embodiments, the composition is started as a 0.1% ointment. After 7 days, the concentration may be increased to 0.25% and subsequently doubled, if necessary, at weekly intervals to a maximum strength of 2%. In some embodiments, a thin layer of ointment is applied once daily to the affected areas for 2-4 weeks. In some embodiments, the ointment is left in place for 10 to 20 minutes before the area is rinsed thoroughly. In some embodiments, the concentration of lipid secretion enhancing thiol-containing agent is gradually increased to a maximum of 5%, and treatment is continued for as long as necessary.

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

One embodiment provides a method for treating meibomian gland dysfunction by administering a topical composition comprising a lipid secretion enhancing thiol-containing agent. One embodiment provides a method for treating meibomian gland dysfunction by administering a topical composition comprising a lipid secretion enhancing thiol-containing agent combined with a keratolytic agent.

In some embodiments, the topical administration of the composition comprising a lipid secretion enhancing thiol-containing agent occurs once a week. In some embodiments, the topical administration of the composition comprising a lipid secretion enhancing thiol-containing agent occurs twice a week. In some embodiments, the topical administration of the composition comprising a lipid secretion enhancing thiol-containing agent occurs every other day. In some embodiments, the topical administration of the composition comprising a lipid secretion enhancing thiol-containing agent occurs every day. In some embodiments, the topical administration of the composition comprising a lipid secretion enhancing thiol-containing agent occurs several times a day.

In some embodiment, the method comprises treatment in an acute treatment scenario. In another embodiment, the method comprises treatment of a patient naïve to similar or identical treatment. In another embodiment, the method comprises treatment in a chronic treatment scenario. In another embodiment, the method comprises treatment in a maintenance therapy scenario. In an acute treatment scenario, the administered dosage of lipid secretion enhancing thiol-containing agent may be higher than the administered dosage of lipid secretion enhancing thiol-containing agent employed in a chronic treatment scenario or a maintenance therapy scenario. In an acute treatment scenario, the lipid secretion enhancing thiol-containing agent may be different from the lipid secretion thiol-containing agent employed in a chronic treatment scenario. In some embodiments, the course of therapy begins in the initial phase of therapy as an acute treatment scenario and later transitions into a chronic treatment scenario or a maintenance therapy scenario.

In certain clinical presentations, patients may require an initial treatment administered by a physician or healthcare professional, either by placing a more highly concentrated composition of one of the therapeutic agents described herein. In the event the higher concentration compositions are required, the application thereof may require ocular shielding or other activity to minimize the impact of irritation or disruption of the ocular surface or surrounding tissues. Following such a procedure, a patient may be given a different composition of active agent to take home to apply periodically to the lid margin to maintain the patency of the meibomian gland. Such application may occur twice daily, once a day, weekly or monthly, depending on the composition activity and the desired product profile of the therapy.

One aspect of the methods of treatment described herein is the location of the topical administration of the composition. In one embodiment, the composition comprising a lipid secretion enhancing thiol-containing agent is administered such that no irritation to eye occurs. In one embodiment, the composition comprising a lipid secretion enhancing thiol-containing agent is administered to the eye lid margin.

One additional embodiment of the methods of treatment described herein is the use of a protective element provided to the eye to avoid irritation to the eye. Although the compositions described herein are generally non-irritating, in some embodiments (e.g., high concentration of agent or when used on a sensitive eye) a protective element provides an additional layer of safety and comfort for the patient. In one embodiment, the composition comprising a lipid secretion enhancing thiol-containing agent is administered while an eye shield is placed on the eye to reduce contact of the agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a lipid secretion enhancing thiol-containing agent is administered while the lid is pulled away from the globe to reduce contact of the agent with the cornea and/or conjunctiva such that reduced irritation to eye occurs.

As used herein, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "bucillamine" refers to a compound having the structure:

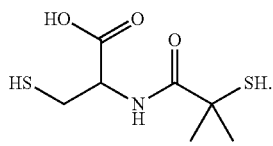

The term "ophthalmically-acceptable carrier" as used herein refers to a carrier that does not cause significant irritation to the eye of an organism when applied in accordance with the teachings of the present invention and does not abrogate the pharmacological activity and properties of an agent carried therewith.

Ophthalmically acceptable carriers are generally sterile, essentially free of foreign particles, and generally have a pH in the range of 5-8. Preferably, the pH is as close to the pH of tear fluid (7.4) as possible. Ophthalmically acceptable carriers are, for example, sterile isotonic solutions such as isotonic sodium chloride or boric acid solutions. Such carriers are typically aqueous solutions contain sodium chloride or boric acid. Also useful are phosphate buffered saline (PBS) solutions.

The term "effective amount" as used herein refers to the amount that is needed to achieve a particular condition, such as increasing lipid secretion from a meibomian gland, lowering the melting point of lipids secreted from a meibomian gland or reducing the viscosity of lipids secreted from a meibomian gland.

The term "therapeutically effective amount" as used herein refers to an amount of a therapeutically effective compound, or a pharmaceutically acceptable salt thereof, which is effective to treat, prevent, alleviate or ameliorate symptoms of a disease. The term "therapeutically effective compound" refers to a compound that is effective to treat, prevent, alleviate or ameliorate symptoms of a disease.

The term "sulfhydryl group" as used herein refers to the —SH functional group.

The term "thiol group" as used herein refers to —C—SH or R—SH group, where R represents an alkane, alkene, or other carbon-containing group of atoms.

The term "ophthalmically-acceptable excipient" as used herein refers to an excipient that does not cause significant irritation to the eye of an organism when applied in accordance with the teachings of the present invention and does not abrogate the pharmacological activity and properties of an agent carried therewith.

The term "keratolytic agent" as used herein refers to a compound which loosens and removes the stratum corneum of the skin, or alters the structure of the keratin layers of skin.

The terms "treat," "treating," or "treatment" as used herein, include reducing, alleviating, abating, ameliorating, relieving, or lessening the symptoms associated with MGD in either a chronic or acute therapeutic scenario. In one embodiment, treatment includes an increase in lipid production. In one embodiment, treatment includes an increase in lipid secretion. In one embodiment, treatment includes a decrease in the viscosity of the lipids secreted.

The term "recurrence," or "reducing relapse" refers to return of MGD symptoms in a chronic therapeutic scenario.

The term "opening" refers to the clearing (at least in part) of an obstructed meibomian gland canal or orifice and/or maintaining the patency of the meibomian gland canal or orifice.

The term "lipid secretion enhancing thiol-containing agent" as used herein refer to a thiol-containing agent that causes increases differentiation of meibocytes or increases proliferation of meibocytes or increases the quantity of lipids secreted from the meibomian glands or alters the composition of meibum lipids.

The term "meibum lipids" as used herein refers to lipids secreted by meibomian gland.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

"Pharmaceutically acceptable salt" includes both acid and base addition salts. A pharmaceutically acceptable salt of any one of the inhibitor of cyclin-dependent kinases (CDKs) compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

EXAMPLES

Example 1: In Vitro Evaluation of the Effect of Thiol Containing Compounds on Lipid Synthesis in a 3D Model Culture of Sebocytes Since secretory cells (meibocytes) of meibomian glands, share similarities with that of the secretory cells (sebocytes) of sebaceous glands, as can be validated from their similar structure, similar function and their joint embryologic development (Knop 2011_IOVS) the effect of Thiol containing Lipids on lipid production can be evaluated in a 3D model culture of Sebocytes. See also: Barrault 2012, Immortalized sebocytes can spontaneously differentiate into a sebaceous-like phenotype when cultured as a 3D epithelium, Exp. Derm, 21:299-319

The effect of different compounds on lipid synthesis was evaluated, in a 3D model culture of Sebocytes. Drug candidates were compounds comprising a thiol group. Selenium disulfide (SeS2 dispersed in CarboxymethylCellulose—CMC) as a positive control. Since Sebocytes differentiation is associated with increased lipid synthesis and accumulation, evaluation of proliferation and differentiation was done by quantifying lipid accumulation in the 3D Sebocytes culture (human cell line—SEBO662). Lipid accumulation was evaluated by lipid staining with Oil red staining.

Sebocytes SEBO662 were cultured into a three dimension (3D) epithelium and differentiated to a sebaceous-like phenotype. The Sebocytes were treated or not (control) with the test compounds and incubated for 14 days. All experiments were performed 3 times. After incubation, tissues were snap-frozen. Formaldehyde-fixed cryo sections were stained using an Oil-red-O solution and counterstained using haematoxylin. For each test condition, the sections were observed using a light microscope equipped with a camera. Five pictures were taken per replicate, making 15 values per treatment condition. The lipid content in each sample was quantified by calculation of the lipid droplet surface area. Quantitative comparison of all data points between lipid's droplet surface area of tested compounds versus control was performed Results FIG. 1 is an illustration of Oil-red-O staining in 3D Sebocytes epithelium for the control.

Figure 2:
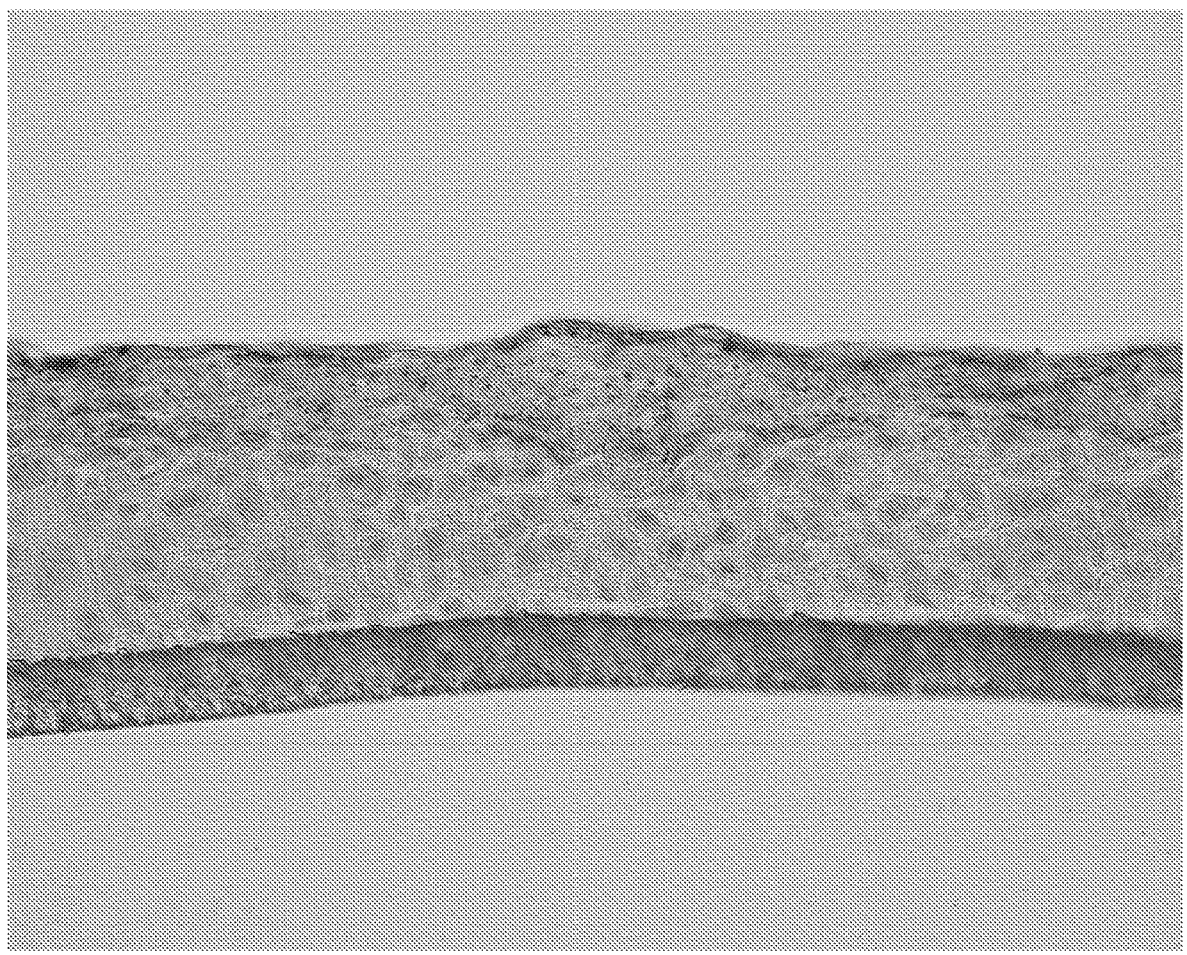
FIG. 2 is an illustration of Oil-red-O staining in 3D Sebocytes epithelium for 1.0 µM bucillamine.

FIG. 2 is an illustration of Oil-red-O staining in 3D Sebocytes epithelium for 1.0 µM bucillamine.

Figure 3:
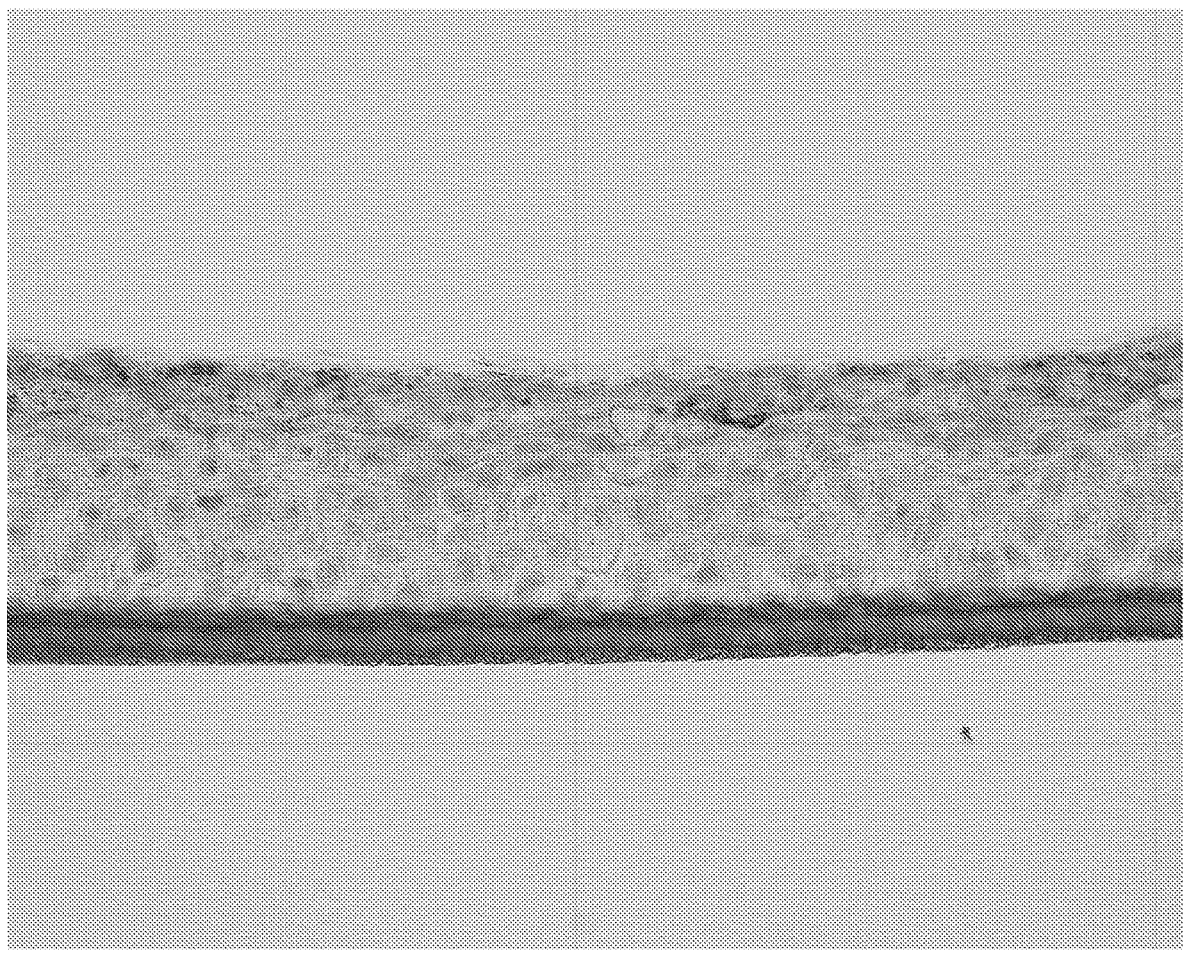
FIG. 3 is an illustration of Oil-red-O staining in 3D Sebocytes epithelium for 0.1 µM bucillamine.

FIG. 3 is an illustration of Oil-red-O staining in 3D Sebocytes epithelium for 0.1 µM bucillamine.

Quantitative Comparison

Selenium disulfide ($SeS_2$), at 0.01 µM and 0.1 µM, induced a statistically significant increase of lipid accumulation, in the upper region of the 3D Sebocytes, at both test concentrations (282% and 348% of the control, respectively).

Bucillamine tested at 0.1 µM and 1 µM induced a statistically significant increase of lipid accumulation in the upper region of the 3D Sebocytes (172% and 214% of the control, respectively). At a concentration of 0.01 µM, a non-significant increase in sebum production (115%) was observed.

Conclusions

Bucillamine at concentrations of 0.1 µM and 1 µM had a significant stimulating effect on lipid synthesis in the 3D Sebocytes model.

Example 2: Evaluation of the Keratolytic Effect of Bucillamine

Dose response and time course analyses was performed initially in order to evaluate the impact of bucillamine on HaCaT cell viability. Then, selected non-toxic concentrations were further evaluated by BrdU incorporation to determine the ability of the test item to reduce the keratinocyte proliferation rate. In addition, the ability of the test items to reduce thiol moieties, and therefore loosen the blockage of the meibomian gland, was tested on stratum corneum obtained from human skin.

Dose Response and Time Course Analyses

Figure 4A:
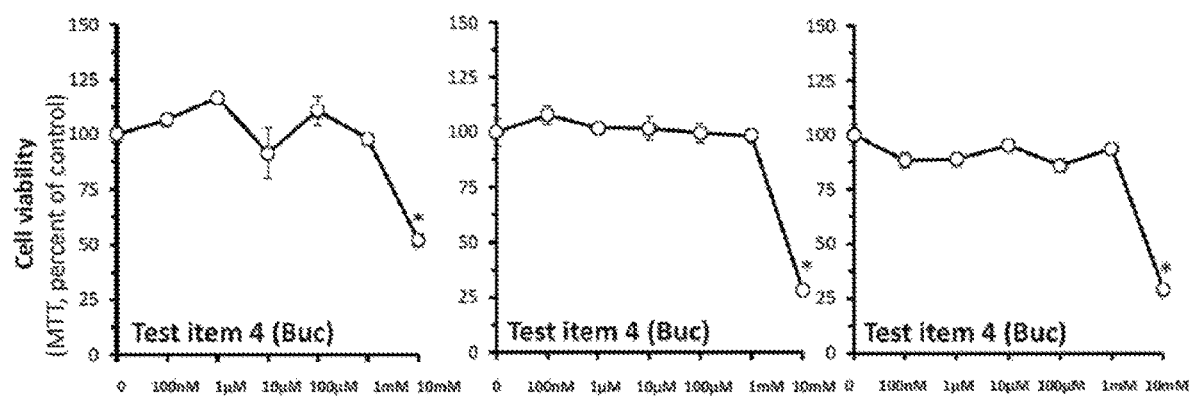
FIG. 4a is an illustration of cell viability in MTT assay upon treatment with bucillamine.

The cells were incubated without or with six concentrations of the test item, for 24, 48 and 72 hr at 37° C. with 5% $CO_2$ under humidified conditions. At the end of each incubation period, cell viability was measured by MTT assay. A blank control was subtracted from all the measurements. The results are provided in FIG. 4a.

HaCaT Turnover Rate Determination

Figure 4B:
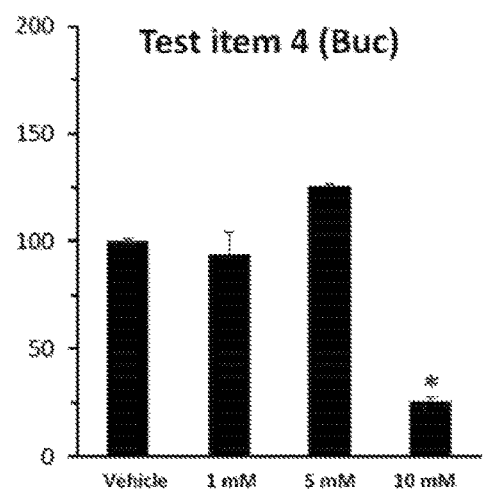
FIG. 4b is an illustration of HaCaTcell proliferation upon treatment with bucillamine.

The proliferation rate of HaCaT cells upon treatments with the test item was examined by using the BrdU assay. Colorimetric evaluation of the turnover rate was recorded by ELISA reader. The results are provided in FIG. 4b.

Ex Vivo Assessment in the Human Skin Model System

The human skin organ culture was obtained from healthy patient undergoing plastic surgery. The study was initiated the day of surgery.

Figure 4C:
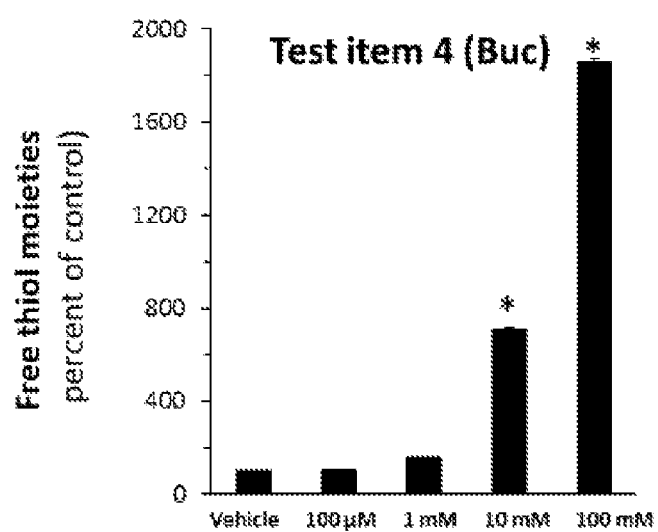
FIG. 4c is an illustration of the free thiol determination in an ex vivo assessment in the human skin model system upon treatment with bucillamine.

To isolate the free thiol from the mixture of the samples, samples were incubated with equal volume of TCA (trichloroacetic acid) for 5 min. Then, the tubes were centrifuge for 15 min at 10,000 rpm at room temperature. The pellets were evaluated. The results are provided in FIG. 4c.

Conclusions

In Vivo—Bucillamine showed keratostatic efficacy by reducing the turnover rate of the keratinocytes cells.

Ex-vivo—Bucillamine demonstrated keratolytic efficacy by the ability to reduce thiol moieties in order to loosen the blockage of the meibomian gland and showed a significant effect in this assay and increased the free thiol moieties by approx. 6-fold at non-toxic concentrations.

Example 3: Preparation of a Pharmaceutical Composition Comprising a Lipid Secretion Enhancing Thiol-Containing Agent 2.5 grams of bucillamine is mixed with 10 grams of liquid paraffin and 87.5 grams of white soft petrolatum and heated to ~60° C. with constant stirring until homogeneous mixture is obtained and cooled to room temperature.

2.5 grams of bucillamine is mixed with 2.5 grams of cholesterol, 10 grams of liquid petrolatum, and 85 grams of Vaseline. The mixture is heated under mixing until all ingredients melt ~80° C. and homogeneity obtained and then cooled to room temperature.

2.5 grams of bucillamine is mixed with 5 grams of squalene and 97.5 grams of Vaseline and heated to ~60° C. with mixing in order to obtain homogeneity and then cooled to room temperature 2.5 grams of bucillamine is mixed with 10 grams of mineral oil, 10 grams of squalene, 10 grams of capric/caprylic triglyceride, 10 grams of microcrystalline wax, 10 grams of hydrogenated vegetable oil, and 3 grams of lanoline and Vaseline to 100 grams. The mixture is heated to ~80-90° C. with mixture until homogeneity is obtained and cooled to room temperature.

2.5 grams of bucillamine is mixed with 3 grams of cholesterol and 10 grams of phospholipids and dissolved in ethanol acetone mixture. The mixture is dried under vacuum and mixed with 1000 ml of saline solution under vigorous agitation following high-pressure homogenization to produce very fine liposome dispersion.

2.5 grams of bucillamine is mixed with 5 grams of hydrogenated vegetable oil and 5 grams of mineral oil and heated to ~80° C. with stirring until all ingredients are melted. 87.5 grams of pre heated water solution to 80° C. comprising 1% tween80 and 2% phospholipids are added under vigorous mixing and high shear homogenization. 0.8 grams of xanthan gum (Xantural 3000™) is added under vigorous mixing and the mixture is cooled to room temperature to obtain solid lipid dispersion.

2.5 grams of bucillamine is dissolved in sterile water for injection, 1.2 grams of xanthan gum and 0.8 grams of sodium chloride are added and the mixture is agitated to produce a clear gel.

Example 4: Increasing Lipid Production in Meibomian Glands

The objective of the study is to evaluate the effect of a lipid secretion enhancing formulations on increasing the quantity of lipids produced by the meibomian glands.

A light layer of lipid secretion enhancing thiol-containing agent is applied to the lower lid of a subject, and the quantity of lipids produced by the meibomian gland is measured before and after application of the agent. An exemplary method to determine the level of lipid production in the meibomian gland is by culturing human meibomian gland epithelial cells with and without the thiol-containing agent for 1, 3, 5 and 7 days and then determining the magnitude of cellular lipid and lysosome accumulation by staining cells with LipidTOX green neutral lipid stain and LysoTracker® Red DND-99 (a fluorescent technique designed for labeling lysosomes). Additionally, by examining whether the thiol-containing agent increases the synthesis of polar and neutral lipid species in human meibomian gland epithelial cells, by culturing cells in media with or without the thiol-containing agent for 7 days and then processing the cells for the identification of phospholipids, and wax and cholesterol esters. These latter 2 species are the predominant lipids in human meibum. The analyses involve the use of high-performance thin-layer chromatography and the quantification of staining intensities with ImageJ dye. Another known alternative method utilizes Oil red O and Nile red staining. The degree of lipid accumulation is determined through the use of Nile Red dye. This dye will give a fluorescent signal which is proportional to the amount of lipids which have been accumulated.

Example 5: Increasing Lipid Secretion from Meibomian Glands

The objective of the study is to evaluate the effect of a lipid secretion enhancing formulation on increasing the quantity of lipids secreted from the meibomian glands.

A light layer of lipid secretion enhancing thiol-containing agent is applied to the lower lid of a subject, and the quantity of lipids secreted from the meibomian gland is measured before and after application of the agent. An exemplary method to determine the level of lipid secretion from the meibomian gland is using a "meibometer" instrument for quantifying meibomian lipid on the lid margin, which is an optical spectrophotometer that has tapes that are put against the lid margin to measure the amount of meibum being secreted (Chew et al, Current Eye Research, Vol. 12 (3), pages 247-254, 1993).

Example 6: Treatment of MGD Patients

The objective of the study is to evaluate the effect of a lipid secretion enhancing formulations on treating MGD or at least one of its symptoms.

A light layer of lipid secretion enhancing thiol-containing agent is applied to the lower lid of an MGD patient, and the severity of MGD or at least one of its symptoms is measured before and after application of the agent. Exemplary methods for assessing and monitoring the severity of MGD or at least one of its symptoms include, but are not limited to, patient questionnaires, meibomian gland expression, tear stability break up time, and determining the number of patent glands as seen by digital expression. Other methods for assessing MGD symptoms, include but are not limited to, Shirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

What is claimed is:

1. A method for increasing lipid secretion from a meibomian gland, comprising topically administering to an eyelid margin of a patient in need thereof an ophthalmic composition comprising an ophthalmic ally-acceptable carrier and a therapeutically effective amount of at least one agent which increases lipogenesis in the meibomian gland or increases lipid secretion from the meibomian gland, wherein the agent comprises (i) bucillamine or a pharmaceutically acceptable salt thereof, or (ii) a compound or a pharmaceutically acceptable salt thereof, having the structure provided below

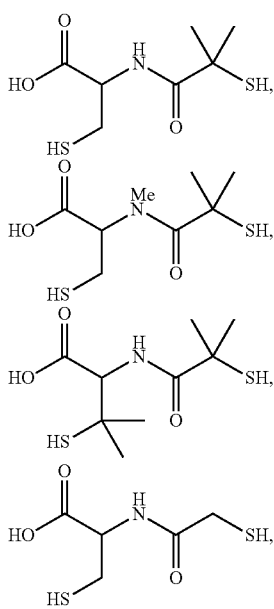

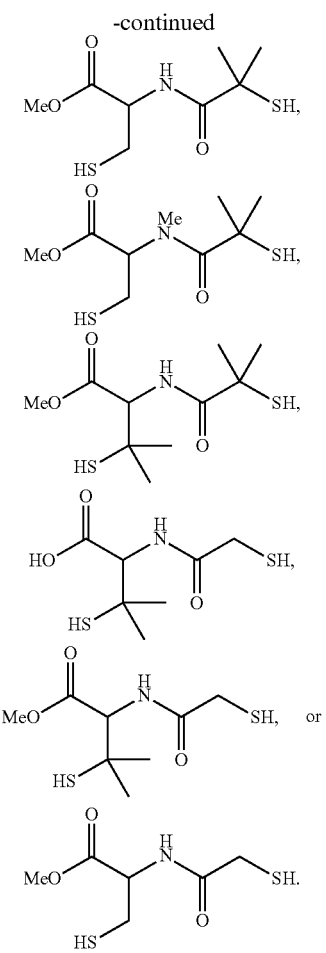

2. The method of claim 1, wherein the ophthalmically-acceptable carrier comprises at least one ophthalmically-acceptable excipient.

3. The method of claim 1, further comprising the step of administering to the patient a keratolytic agent.

4. The method of claim 3, wherein the keratolytic agent is selected from the group consisting of benzoyl peroxide, coal tar, dithranol, salicylic acid, selenium disulfide, alpha-hydroxy acid, urea, boric acid, retinoic acid, lactic acid, sodium thioglycolate or allantoin.

5. The method of claim 1, wherein the composition comprises between about 0.01% weight per weight (w/w) to about 10% w/w of the agent.

6. The method of claim 5, wherein the composition comprises about 2.5% w/w of the agent.

7. The method of claim 1, wherein the composition comprises between about 0.1 µM to about 1 µM of the agent.

8. The method of claim 1, wherein the composition is an ointment, cream, lotion, or gel.

9. The method of claim 1, wherein the composition is a dispersion, suspension, or emulsion.

10. The method of claim 1, wherein the composition comprises paraffin, petrolatum, squalene, microcrystalline wax, lanoline, cholesterol, mineral oil, vegetable oil, a triglyceride, phospholipids, or a combination thereof.

11. The method of claim 4, wherein the keratolytic agent is selenium disulfide.

12. The method of claim 1, wherein the patient is suffering from meibomian gland dysfunction.

13. The method of claim 12, wherein the meibomian gland dysfunction is characterized by an obstruction of the meibomian gland.

14. The method of claim 1, wherein the effective amount of the at least one agent increases meibum lipid secretion from the meibomian gland.

15. The method of claim 1, wherein the at least one agent comprises bucillamine.

16. The method of claim 1, wherein the at least one agent is bucillamine.

* * * * *